United States Patent [19]

Lex

[11] 3,931,184
[45] Jan. 6, 1976

[54] PURIFICATION METHOD FOR PROLYL-LEUCYLGLYCINAMIDE

[75] Inventor: Charles George Lex, Kenosha, Wis.

[73] Assignee: Abbott Laboratories, North Chicago, Ill.

[22] Filed: Oct. 31, 1974

[21] Appl. No.: 519,463

[52] U.S. Cl............................................ 260/112.5 R
[51] Int. Cl.$^2$.................... C07C 103/52; C07G 7/00
[58] Field of Search .......... 260/112.5; 424/177, 274

[56] References Cited
UNITED STATES PATENTS

| | | | |
|---|---|---|---|
| 3,708,593 | 1/1973 | Plotnikoff | 424/274 |
| 3,795,738 | 3/1974 | Plotnikoff | 424/274 |

OTHER PUBLICATIONS

Nair et al.: Biochem. Biophys. Res. Comm., 43, 1376–1381 (1971).

*Primary Examiner*—Lewis Gotts
*Assistant Examiner*—Reginald J. Suyat
*Attorney, Agent, or Firm*—Paul D. Burgauer; Robert L. Niblack

[57] ABSTRACT

The tripeptide L-prolyl-L-leucylglycinamide can be obtained in pure, crystalline form by dissolving it in methanol and adding to a clear methanol solution thereof, a relatively large volume of diethyl ether. The obtained tripeptide shows essentially only a single spot on TLC plates.

2 Claims, No Drawings

PURIFICATION METHOD FOR PROLYL-LEUCYLGLYCINAMIDE

DETAILED DESCRIPTION OF THE INVENTION

The tripeptide L-prolyl-L-leucylglycinamide, hereinafter referred to as MIH for melanocite inhibiting hormone, has recently been shown to be a useful drug for combating depression and the symptoms of Parkinsonism when administered to warm-blooded animals afflicted with such symptoms. Recently issued, U.S. Pat. Nos. 3,708,593 and 3,795,738 show the specific benefits of this material upon oral administration to warm-blooded animals.

However, unfortunately, medicinally pure material is rather difficult to obtain. Chemically, there is no difficulty in preparing this tripeptide and to obtain it in relatively pure crystalline form by crystallizing it from water. While material obtained in this fashion is usually satisfactory for investigation of the effects of the drug, it is necessary to obtain a truly pure form of the material for pursuit of the drug in the medical treatment of humans. While material known to date may analyze properly from the carbon, hydrogen and nitrogen content of the assigned structure of the hemihydrate of MIH, thin-layer chromatography shows that the material recrystallized several times from water still contains impurities, often exceeding 2% by weight. A major proportion of these impurities is N-carbonbenzoxy-MIH, which has solubility characteristics so similar to MIH that recrystallization by previous methods will not remove it.

It is thus an object of the present invention to prepare MIH that shows essentially only a single spot upon thin-layer chromatography. It is a particular object of this invention to purify MIH to a chemically and physically substantially pure form.

These and other objects are accomplished upon crystallizing MIH by dissolving one part by weight thereof in at least three parts by weight of methanol and adding at least the fourfold volume of ether thereto. Crystals of highest purity of the hemihydrate of MIH are obtained in this manner. They show only a single spot on thin-layer chromatography from the customary solvents or solvent mixtures.

In a more specific embodiment, one kilogram part of MIH hemihydrate is dissolved in 3 – 4 liter parts of methanol; the solution is filtered after all or most of the MIH has been dissolved and about 12 – 15 liter parts of diethyl ether are added to the filtrate. Upon standing, crystals of MIH hemihydrate appear within about 30 minutes at room temperature, and after cooling this mixture to near 0°, essentially all of the initially present MIH is obtained in pure form.

In order to illustrate the process of this invention, reference is made to the following example which, however, is not meant to limit the invention in any respect.

EXAMPLE

A solution of 1.8 kg. of the hemihydrate of L-prolyl-L-leucylglycinamide in 5.4 liters of methanol is prepared by stirring these materials at 20° – 25° C. for a period of 45 minutes. The solution is then filtered. While stirring the filtrate, 21.6 liters of diethyl ether is added in small portions over a period of about 15 minutes. Crystallization begins soon after agitation is stopped. After standing for 30 minutes, agitation is restarted, another 10.8 liters of ether is added in small aliquots over a 5-minute period. Agitation is stopped at this point and the mixture is allowed to stand for 16 hours near 0° C. The white, crystalline material is collected by filtration, washed with ether and dried at room temperature in an evacuated chamber to yield 1.48 kg. of the hemihydrate of MIH, representing 82% of theory. The material passes all established chemical and physical specifications, including analysis.

The following table shows a comparison of the starting material of the above example with the final product with the starting material having been crystallized from water in the usual known fashion. In all instances, the term MIH is to be understood as MIH hemihydrate.

TABLE

| | Starting Material | End Product |
|---|---|---|
| Melting Point | 117.5–123.5° | 121–122° C. |
| Assay | 98.3% | 99.3% |
| $[\alpha]_D^{25}$ (C=1; H$_2$O) | –56.4° | –56.6° |
| TLC* | Major R$_f$ 0.77 | Major R$_f$ 0.78 |
| | Minor R$_f$ 0.84 } >2% | No impurities detected |
| | Minor R$_f$ 0.91 | |

*TLC = thin-layer chromatography, using chloroform/methanol/ammonia 2:2:1 as the solvent. Upon replacing ammonia with acetic acid, no impurities are found in the end product either. The plates are visualized by ninhydrin and Cl$_2$-tolidine.

Obviously, those skilled in the art will recognize that the ether can be added in smaller or larger portions, most of it at room temperature before, during or after stirring with more to be added subsequently before, during or after cooling the mixture to near 0°. The upper volume limit of ether is unlimited except that economic considerations would limit this to about 20 parts by volume per weight part of MIH. At least 8 parts per volume of the ether should be used in order to force crystallization of the major portion of the MIH. Less than three parts by volume of methanol reduces the efficiency of this system in that not all of the MIH will go into solution except upon heating while excessive amounts of methanol, i.e., above four parts by volume per weight part of MIH only increases the total volume unnecessarily and requires subsequently larger amounts of ethyl ether.

The new method produces highly desirable, crystalline, pure material from a crude material or a prepurified, water-recrystallized MIH. The new method has the advantage of yielding MIH in crystalline form and to do this without requiring any heating, be it for dissolving the MIH or be it to reduce the solvent volume to insure good recovery yields. To this extent, the new purification method is far superior over any method requiring water as the crystallization solvent since in that instance, the initial aqueous solution has to be heated to get most of the desirable tripeptide into solution, to concentrate the aqueous solution and, after removing the crystals from the cooled solution, excessive time or heat is required to drive off any traces of water still associated with the crystals.

What is claimed is:

1. The process of purifying the crude tripeptide L-prolyl-L-leucylglycinamide consisting essentially in dissolving 1 part by weight of said tripeptide in at least about 3 parts by volume of methanol, adding at least 12 parts by volume of diethyl ether to said solution, and crystallizing said tripeptide at a temperature of 0° – 25° C.

2. The process of claim 1 wherein 3 – 4 parts by volume of methanol are used to dissolve one part by weight of said tripeptide and said solution is filtered before adding said ether.

* * * * *